United States Patent
O'Neil

(10) Patent No.: US 7,150,739 B2
(45) Date of Patent: Dec. 19, 2006

(54) CATHETER SYSTEM AND METHOD FOR DELIVERING MEDICATION TO THE BLADDER

(75) Inventor: Alexander George Brian O'Neil, Subiaco (AU)

(73) Assignee: Go Medical Industries Pty, Ltd., Western (AU)

( * ) Notice: Subject to any disclaimer, the term of this patent is extended or adjusted under 35 U.S.C. 154(b) by 547 days.

(21) Appl. No.: 10/686,026

(22) Filed: Oct. 15, 2003

(65) Prior Publication Data

US 2004/0171979 A1 Sep. 2, 2004

Related U.S. Application Data

(60) Provisional application No. 60/419,063, filed on Oct. 15, 2002.

(51) Int. Cl.
*A61M 1/00* (2006.01)
(52) U.S. Cl. ..................... 604/540; 604/644
(58) Field of Classification Search ............ 604/93.01, 604/171, 172, 174, 185, 255, 248, 500, 514, 604/517, 540, 257, 544, 261–263, 403, 408, 604/409, 410, 906, 911, 96.01, 97.01, 98.01, 604/98.02, 99.01–99.04; 600/33–35
See application file for complete search history.

(56) References Cited

U.S. PATENT DOCUMENTS

| | | | |
|---|---|---|---|
| 3,672,372 A * | 6/1972 | Heimlich | 604/544 |
| 3,894,540 A * | 7/1975 | Bonner, Jr. | 604/171 |
| 4,140,127 A * | 2/1979 | Cianci et al. | 604/171 |
| 4,148,319 A | 4/1979 | Kasper et al. | |
| 4,197,848 A | 4/1980 | Garrett et al. | |
| 4,284,081 A | 8/1981 | Kasper et al. | |
| 4,423,741 A * | 1/1984 | Levy | 600/581 |
| 4,652,259 A | 3/1987 | O'Neil | |
| 4,722,731 A | 2/1988 | Vailancourt | |
| 4,805,611 A * | 2/1989 | Hodgkins | 128/207.14 |
| 5,007,897 A | 4/1991 | Kalb et al. | |
| 5,100,396 A * | 3/1992 | Zamierowski | 604/305 |
| 5,114,398 A | 5/1992 | Trick et al. | |

(Continued)

FOREIGN PATENT DOCUMENTS

WO  WO 02/064195 A2  8/2002

OTHER PUBLICATIONS

International Search Report from corresponding International Application No. PCT/AU03/01361 date Dec. 2, 2003.

*Primary Examiner*—Cris L. Rodriguez
(74) *Attorney, Agent, or Firm*—Alston & Bird LLP

(57) ABSTRACT

An improved urinary catheter device having a urine collection bag selectively drains the bladder or provides a fluid pathway to the bladder for injecting an amount of medication therein. A multi-position valve can be manipulated from a position in which fluid is allowed to drain into the catheter bag to a position in which a fluid delivery pathway is provided to the bladder. In one embodiment a fluid delivery device is connected to the fluid delivery pathway provided. The fluid delivery device can be pressurized so that manipulation of the multi-position valve results in the fluid contents of the fluid delivery device being forced into the patient's bladder. A method for using the device drains the bladder of a patient into the catheter bag, and manipulates the valve to inject an amount of medication into the patient's bladder without opening or piecing the catheter bag.

18 Claims, 7 Drawing Sheets

U.S. PATENT DOCUMENTS

| | | | |
|---|---|---|---|
| 5,116,309 A | 5/1992 | Coll | |
| 5,125,893 A * | 6/1992 | Dryden | 604/500 |
| 5,147,341 A * | 9/1992 | Starke et al. | 604/349 |
| 5,181,913 A | 1/1993 | Erlich | |
| 5,234,409 A | 8/1993 | Goldberg et al. | |
| 5,242,398 A * | 9/1993 | Knoll et al. | 604/103.05 |
| 5,405,336 A * | 4/1995 | Austin et al. | 604/534 |
| 5,417,657 A | 5/1995 | Hauer | |
| 5,421,334 A | 6/1995 | Jabba | |
| 5,439,452 A | 8/1995 | McCarty | |
| 5,489,281 A * | 2/1996 | Watanabe et al. | 604/317 |
| 5,582,599 A * | 12/1996 | Daneshvar | 604/263 |
| 5,688,239 A | 11/1997 | Walker | |
| 5,855,567 A * | 1/1999 | Reesemann | 604/171 |
| 5,871,475 A | 2/1999 | Frassica | |
| 5,989,230 A | 11/1999 | Frassica | |
| 6,004,305 A * | 12/1999 | Hursman et al. | 604/328 |
| 6,045,542 A * | 4/2000 | Cawood | 604/327 |
| 6,053,905 A * | 4/2000 | Daignault et al. | 604/544 |
| 6,090,069 A | 7/2000 | Walker | |
| 6,096,013 A | 8/2000 | Hakky et al. | |
| 6,102,888 A | 8/2000 | Walker | |
| 6,110,099 A | 8/2000 | Benderev | |
| 6,146,360 A | 11/2000 | Rogers et al. | |
| 6,171,298 B1 | 1/2001 | Matsuura et al. | |
| 6,183,461 B1 | 2/2001 | Matsuura et al. | |
| 6,283,940 B1 | 9/2001 | Mulholland | |
| 6,293,923 B1 | 9/2001 | Yachia et al. | |
| 6,379,334 B1 | 4/2002 | Frassica | |
| 6,398,718 B1 | 6/2002 | Yachia et al. | |
| 6,416,496 B1 | 7/2002 | Rogers et al. | |
| 6,428,467 B1 | 8/2002 | Benderev | |
| 6,470,219 B1 | 10/2002 | Edwards et al. | |
| 6,578,709 B1 * | 6/2003 | Kavanagh et al. | 206/364 |
| 6,602,244 B1 * | 8/2003 | Kavanagh et al. | 604/544 |
| 6,793,651 B1 * | 9/2004 | Bennett et al. | 604/544 |
| 6,887,230 B1 * | 5/2005 | Kubalak et al. | 604/544 |
| 6,979,313 B1 * | 12/2005 | Meek et al. | 604/98.01 |
| 7,001,370 B1 * | 2/2006 | Kubalak et al. | 604/544 |
| 2002/0052576 A1 | 5/2002 | Massengale | |
| 2003/0040708 A1 | 2/2003 | Rogers et al. | |
| 2003/0040709 A1 | 2/2003 | Mason | |
| 2004/0163980 A1 * | 8/2004 | Tanghoj et al. | 206/363 |

* cited by examiner

Fig_3

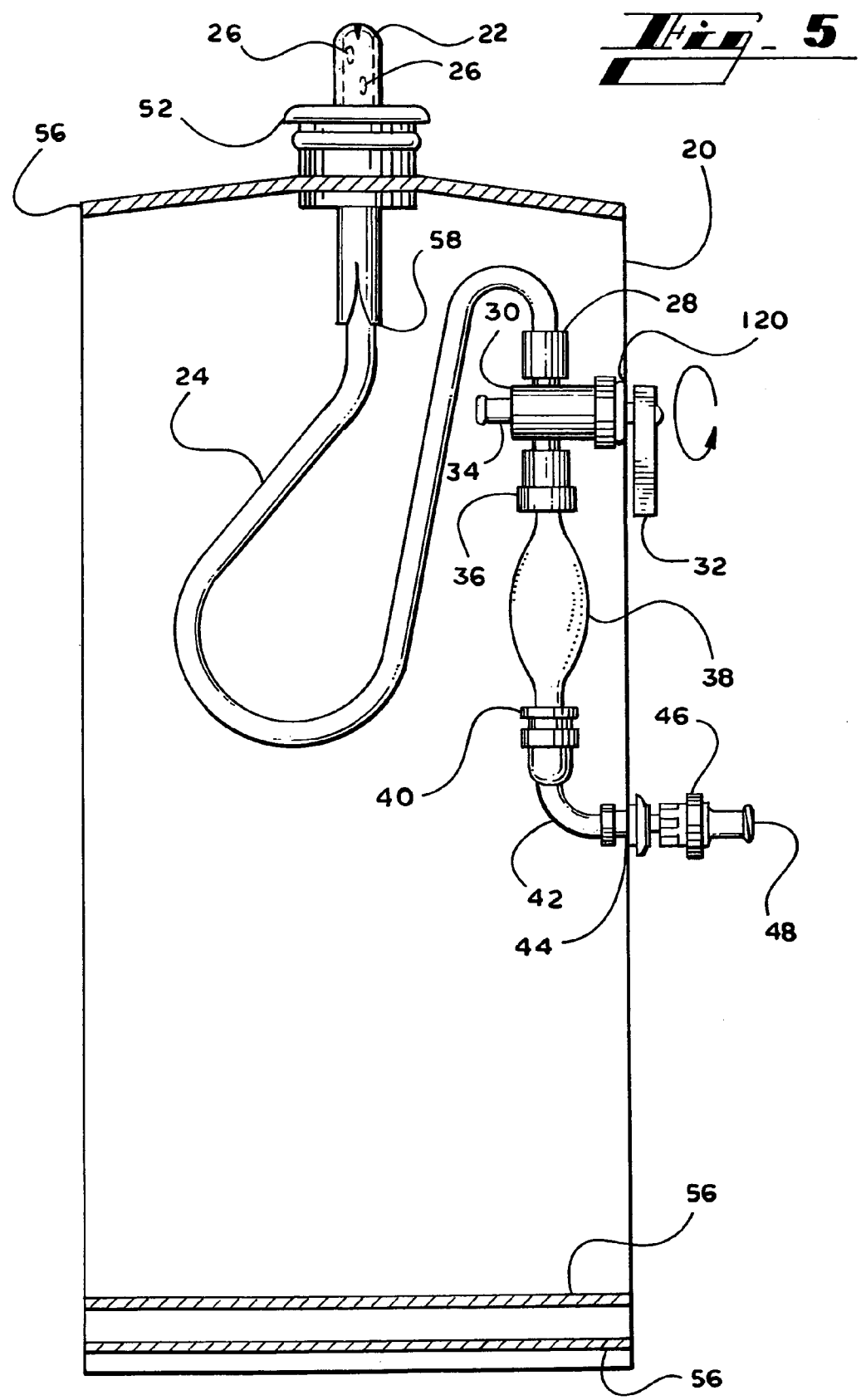
Fig_5

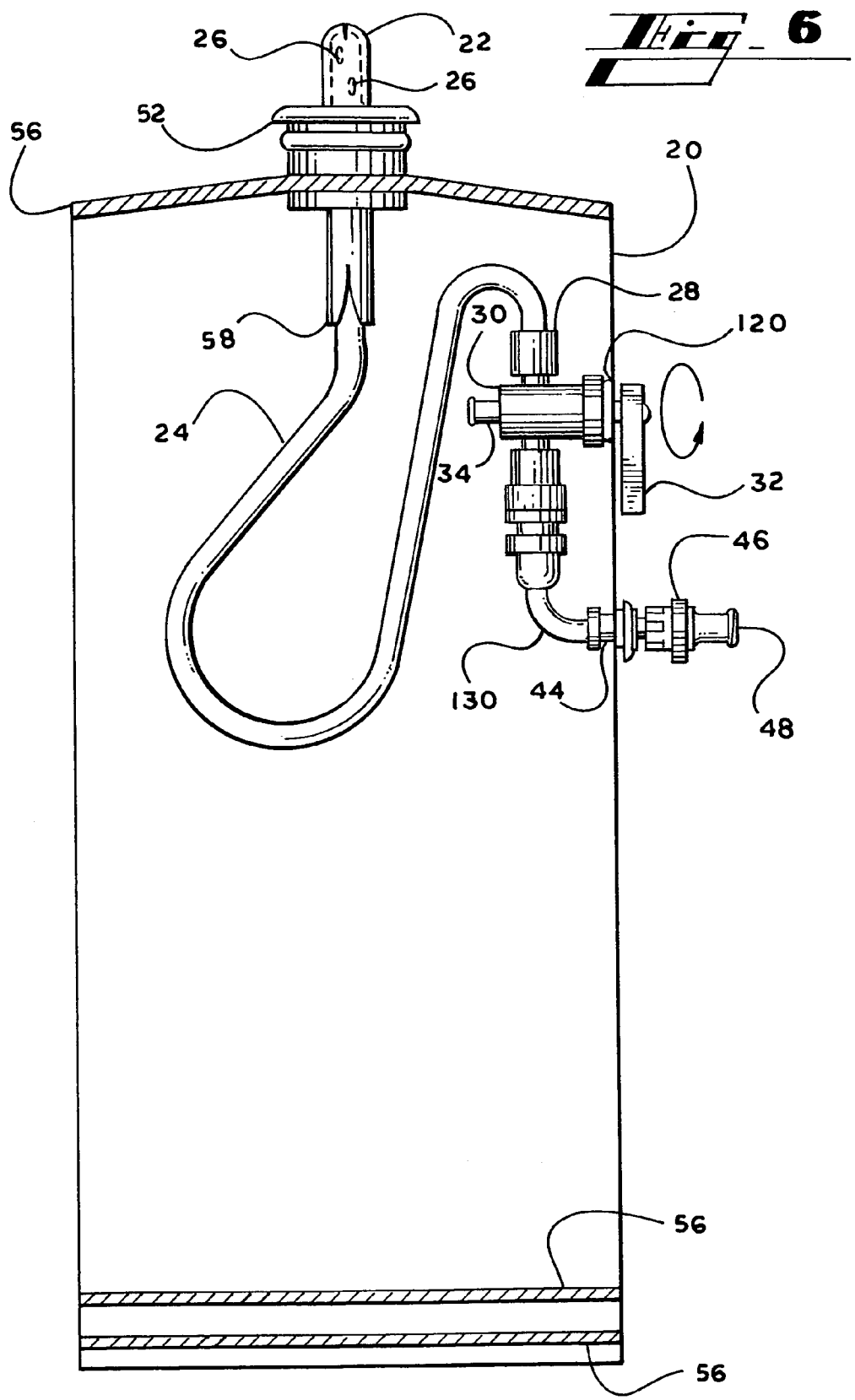

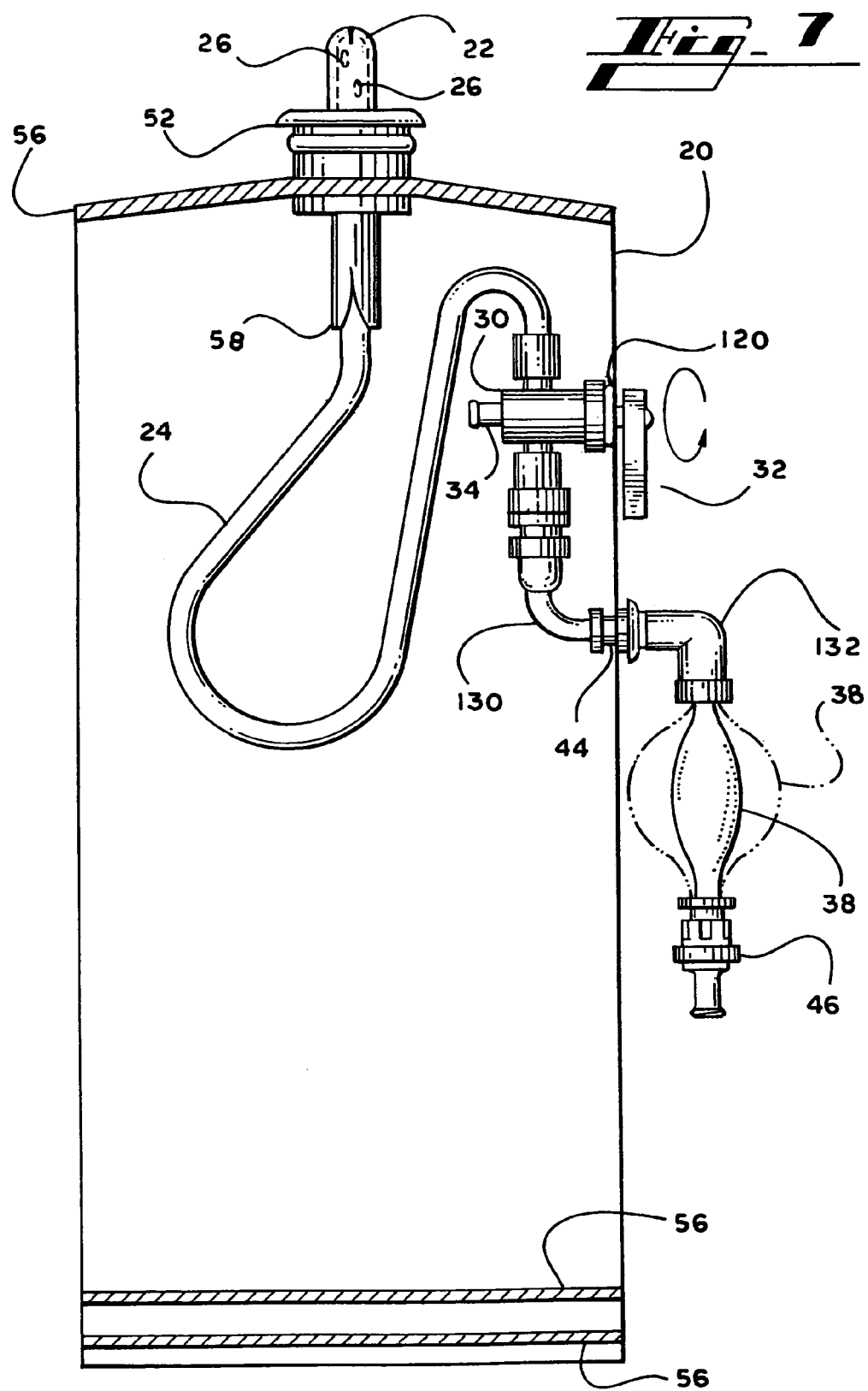

CATHETER SYSTEM AND METHOD FOR DELIVERING MEDICATION TO THE BLADDER

CROSS-REFERENCE TO RELATED APPLICATIONS

This application claims benefit of co-pending U.S. Provisional Patent Application No. 60/419,063 filed on Oct. 15, 2002, titled "Catheter System and Method of Delivering Medication to the Bladder," which is incorporated herein by reference.

BACKGROUND OF THE INVENTION

Urinary tract infections are commonly treated thorough the use of orally administered antibiotics. Because of systematic absorption and other effects, only a small amount of the drugs ingested actually reach the bladder. Therefore, the dosage of these orally administered antibiotics must be chosen such that an effective amount of the drugs will travel to the bladder. As a result of the high dosages used, the antibiotics kill helpful flora in the intestine and are more likely to allow resistant organisms to grow there. It would therefore be advantageous to introduce the medications directly to the bladder.

Prior art methods of introducing drugs into the bladder require the use of a syringe and access to the end of a catheter. Because care must be taken to maintain a sterile environment so that infection does not occur, sterile gowns and gloves are required. As such, these prior art methods are not easily performed outside of a clinical environment. In addition, the prior art methods may not be able to be self administered, particularly by those with certain disabilities (for example, paraplegic patients who typically have trouble with urinary tract infections). Furthermore, it has been impossible to introduce drugs into the bladder through a bagged catheter, such as the type described in U.S. Pat. No. 4,652,259 to O'Neil, because the bag prevents access to the end of the catheter.

Silicone balloons have been used infrequently in the past to deliver intravenous fluids, such as local anesthetics, through a small diameter resistor at a low rate.

Therefore, a need exists in the art for a new system and method of delivering drugs to a patient's bladder. A method is needed through which drugs can easily be introduced to the bladder of a patient outside of a clinical environment while minimizing the risk of infection. Ideally, patients would be able to self-administer the method to introduce drugs to their own bladder safely and conveniently.

BRIEF SUMMARY OF THE INVENTION

The present invention is a device and method of using the same for delivering fluid to the bladder with minimal risk of introducing organisms to the bladder. The invention modifies a prior art catheter having a urine collection container, such as the type described in U.S. Pat. No. 4,652,259, which is incorporated herein by reference, to allow injection of drugs into the bladder for purposes such as stopping or inhibiting bacteria growth there, affecting muscle action, or other purposes for administering medication to the bladder.

A method and system according to the invention deliver drugs into a patient's bladder through a bagged catheter. A system according to the invention is capable of engaging a fluid delivery device associated with the catheter and positioned to preserve sterility of the device so that the possibility of introducing bacteria into the bladder through catheterization is minimized. The fluid delivery device can be positioned, for example, within the urine collection bag. A valve or tap in fluid connection with the fluid delivery device allows the function of the catheter to be switched from draining urine from the bladder into the bag, to delivering drugs into the bladder.

Generally described, a device according to the present invention comprises a container defining an interior portion, the container having at least one opening; a tube having a first end and a second end, the first tube end slideably passing through the opening of the container, the second tube end being disposed within the interior portion of the container; and a valve at least partially disposed within the interior portion of the container, the valve having at least three ports, a first port being connected to the second tube end, a second port being open to the interior portion of the container; and a third port, the valve being operable from outside of the container to selectively open a fluid pathway between the third port of the valve and the first port of the valve. In a preferred embodiment, the device includes a fluid storage cavity connected to the third port of the valve, which is disposed completely within the interior of the container. The fluid storage cavity preferably is capable of delivering fluid under pressure and may be, for example, a balloon or a syringe or a deformable container from which fluid can be squeezed.

The device may optionally be fitted with a second tube having first and second ends, the second tube being a fill tube, with its first end connected to the fluid storage cavity, and its second end being in fluid communication with a source of fluid outside of the container. In this embodiment, a second valve may be connected to the second end of the fill tube, the second valve being a one-way valve to allow fluid to pass into, but not out of the fluid storage device.

The present invention also comprises a kit containing both bagged catheters equipped to delivery medication into a patient's bladder and bagged catheters of the type that only drain the bladder.

A method according the the present invention generally comprises providing a catheter having a tube and a bag, a first end of the tube being in the bag; inserting a second end of the tube into a patient's urethra; draining the patient's bladder into the bag through the tube; injecting a volume of fluid into the patient's bladder through the tube without piercing the bag, and without removing the first end of the tube from the bag.

Other objects, features and advantages of the invention in its various aspects will become apparent upon review of the following description of embodiments of the invention, when taken in conjunction with the drawing and the appended claims.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 5 shows an embodiment of the present invention wherein the valve lever is positioned outside of the bag.

FIG. 6 shows an embodiment of the present invention wherein the valve lever is positioned outside of the bag and a direct fluid pathway to the valve is provided.

FIG. 7 shows an embodiment of the present invention wherein the fluid storage and delivery device is positioned outside of the catheter bag.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
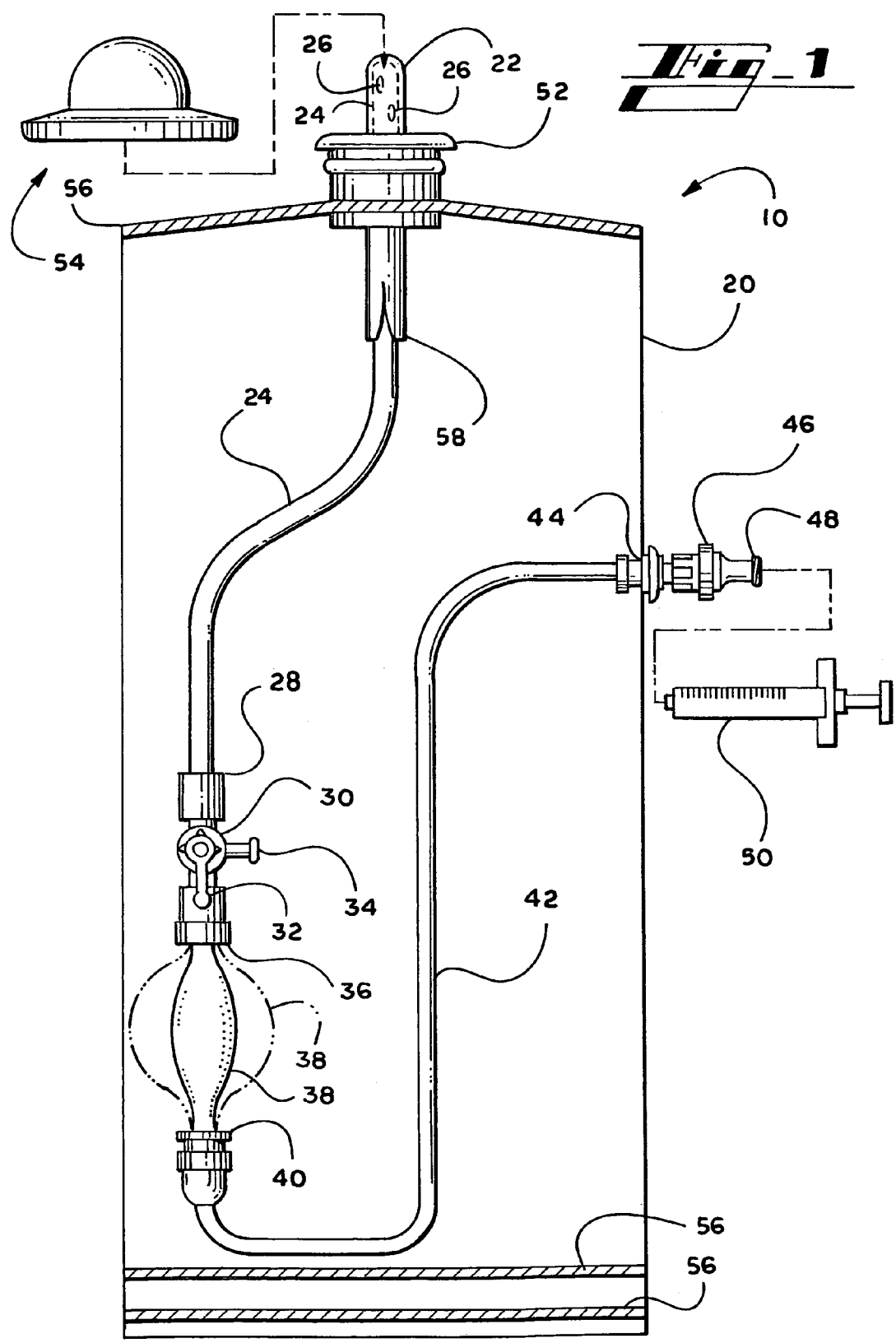
FIG. 1 shows a preferred embodiment of a catheter device according to the present invention.

Referring to FIG. 1, a catheter device 10 according to a preferred embodiment of the invention is shown. This embodiment of the invention adds to an O'Neil catheter, (described in U.S. Pat. No. 4,652,259, named for its inventor) a balloon, syringe, energy storing cavity, or other fluid storage and delivery device that is able to store and deliver an amount of liquid. An O'Neil introducer collar 52 is attached to the catheter bag 20. Catheter bag 20 can be formed of a plastic sleeve having seals 56 at its ends. One end of catheter tube 24 slides into a flange 58, through the collar 52 and out of an introducer tip 22. This end of the catheter tube 24 may have a blunt open end, but the tip of the tube end is preferably rounded for easier insertion into a patient's urethra and bladder. Fluid can flow from a patient's bladder into the catheter tube 24 via tube orifices 26 which are positioned on the walls of the tube. The opposing end of catheter tube 24 is connected to a port 28 on multi-position valve 30. The catheter tube 24 should have sufficient length to reach a patient's bladder from the urethra when the catheter tube 24 is at its maximum extension. Maximum extension of the catheter tube 24 is achieved by sliding the catheter tube 24 through flange 58, collar 52, and out tip 22, until contact between port 28 and flange 58 prevents further extension. To accomplish the sliding of the tube 24, a user can grasp the tube between the walls of the bag 20 with one hand while holding the collar with the other hand, and manipulate the tube because the walls of the bag are flexible.

A fluid storage and delivery device 38 is connected to another port 36 of the multi-position valve 30. The fluid storage and delivery device can store and deliver fluid medications and the like to the bladder of a patient. Yet another port 34 of multi-position valve 30 is open to the interior of catheter bag 20. The operation of the multi-position valve 30 is controlled by a valve lever 32. Rotation of the valve lever 32 with respect to the body of the multi-position valve 30 opens and closes fluid pathways inside the multi-position valve 30. The valve lever 32 can be operated by manipulation without opening or piercing the catheter bag 20. This is desirable as opening or piercing the catheter bag 20 would compromise the sterility of the device. The valve 30, in one position, allows urine to drain from the catheter tube 24 through the port 34 into the catheter bag 20 for catheterization. In another position, this valve closes the path from the catheter tube 24 to the catheter bag 20 and opens a path from the fluid storage and delivery device 38 through ports 36 and 28 to the catheter tube 24 allowing for the fluid to be introduced from the fluid storage and delivery device 38 into the bladder. The fluid storage and delivery device 38 is preferably under mechanical pressure, whether from the elastic properties of a balloon material if a balloon is used, spring loading in the case of a syringe, or other energy storage mechanism. The pressurization allows for a more convenient method of drug delivery, however, manual pressure (e.g. squeezing of a non-pressurized vessel or operation of a non-spring-loaded syringe) is within the scope of the invention.

In the embodiment depicted in FIG. 1, a balloon is used as the fluid storage and delivery device 38 where the dashed lines represent a filled balloon. The balloon is made of an elastomeric material (for example, silicone). The fluid to be delivered to the bladder is stored in the balloon under pressure. This pressure must be great enough to overcome the pressure of the bladder so that the fluids in the balloon flow into the bladder upon operation of the valve. Such balloons are known to lose pressure at the rate of approximately 1–2% per month. Therefore, the invention, in some embodiments, may allow for the filling of the balloon at a time after manufacture or just prior to use.

A fill tube 42 extends from a connection point 40 at the fluid storage and delivery device 38 to pass-through connector 44 located on the wall of the catheter bag 20. The pass-through connector 44 provides a fluid tight seal at the wall of the catheter bag 20. The end of the pass-though connector 44 that is outside of the catheter bag connects to a one-way valve 46. A syringe 50 or other device allowing a volume of fluid to be supplied under pressure may be connected to one-way valve 46 to fill the fluid storage and delivery device 38. The one-way valve 46 allows fluid flow into, but not out of, the fluid storage and delivery device 38. The diameter of the fill tube 42 is preferably less than that commonly used for urinary catheter tubes such as catheter tube 24 to minimize the volume of fluid potentially trapped in the fill tube 42 after filling of the fluid storage and delivery device 38. The length of the fill tube should be sufficient to allow the catheter tube 24 to reach its maximum extension, and is at least as long as the distance from the connector to the connection point 40 when the valve 30 is as close as possible to the flange 58. The necessary length of the fill tube 42 in this embodiment will depend on the location where pass-through connector 44 is mounted to the catheter bag 20. The one-way valve is preferably positioned in the fluid pathway as described to prevent fluid left in the fill tube 42 from draining through the pass-through connector 44. However, it should be realized that the one-way valve could be positioned at any point between the fluid storage and delivery device 38 and the pressure introducing apparatus. The connector 48 associated with the one-way valve 46 (and any other releasable connector described herein) may be a conventional connector such as a luer lock connector as is known in the medical art. When the fluid storage and delivery device 38 comprises a balloon chamber, the liquid pressure introduced, for example, by a syringe 50 will cause the walls of the balloon to expand elastically. Thus, when the filling procedure is complete, the fluid medication in the balloon will remain under pressure.

The fluid storage and delivery device 38 is not required to be a balloon. Other configurations are possible, such as a spring-loaded syringe, or a container having a deformable volume that can be squeezed to expel the liquid contained therein. In the latter case, the fluid within the deformable container need not be under pressure.

Figure 2:
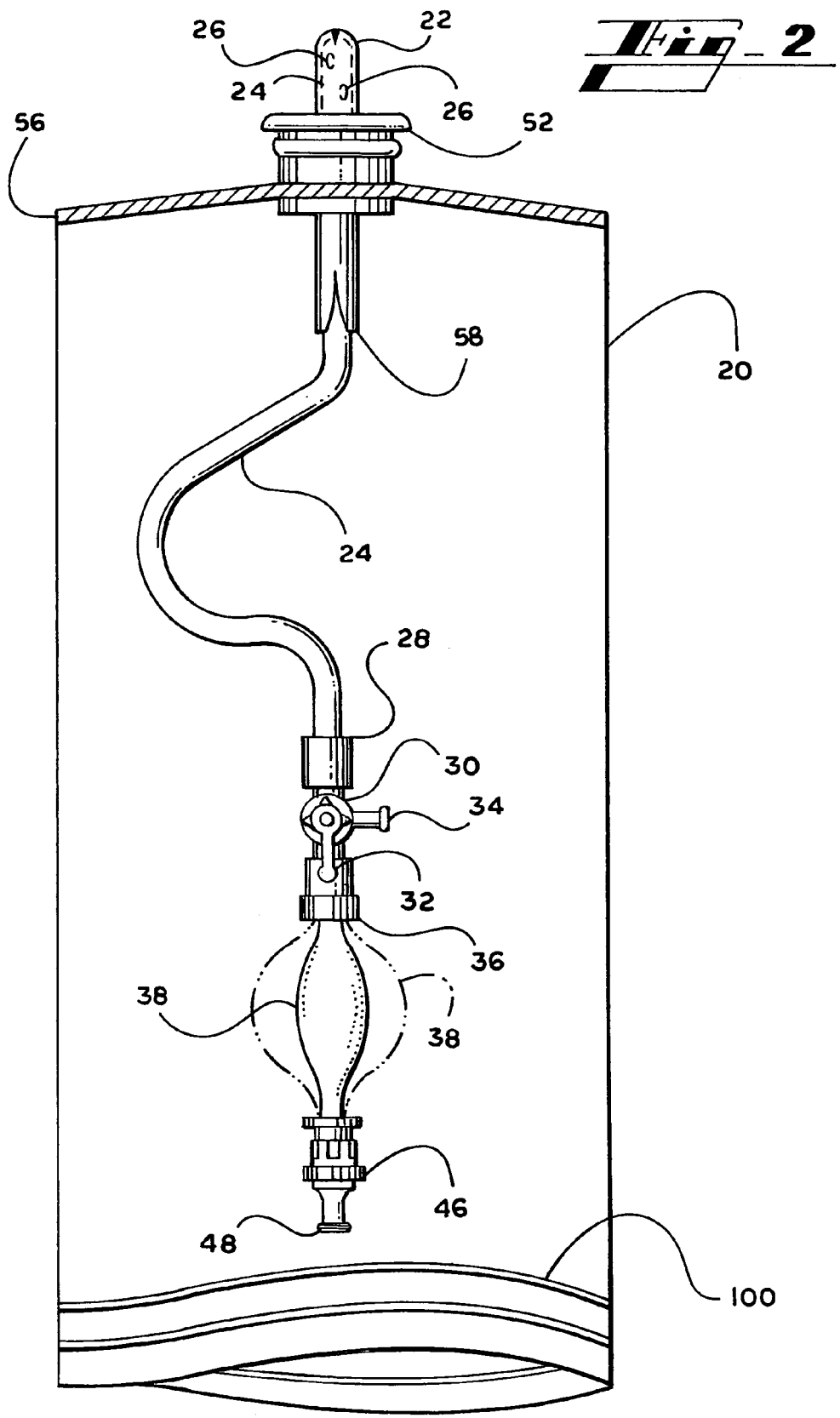
FIG. 2 shows an embodiment of the present invention incorporating a resealable catheter bag.

In another embodiment of the invention, as shown in FIG. 2, a resealable bag is used. A fluid tight seal 100 that can be opened and resealed provides access to a connector 48 on one-way valve 46. In this embodiment, one-way valve 46 is connected to the fluid storage and delivery device 38. The resealable fluid tight seal 100 gives access to the fluid storage and delivery device 38 for filling by an appropriate person in a preferably sterile environment (for example, a pharmacist in a hospital pharmacy). The resealable fluid tight seal 100 would consist of, for example, a reusable seal of the "zip-lock" type or other known resealable, liquid-tight seals. Although the reusable seal is shown positioned at the bottom of catheter bag 20, the reusable seal could be positioned at other locations on the catheter bag 20.

Figure 3:
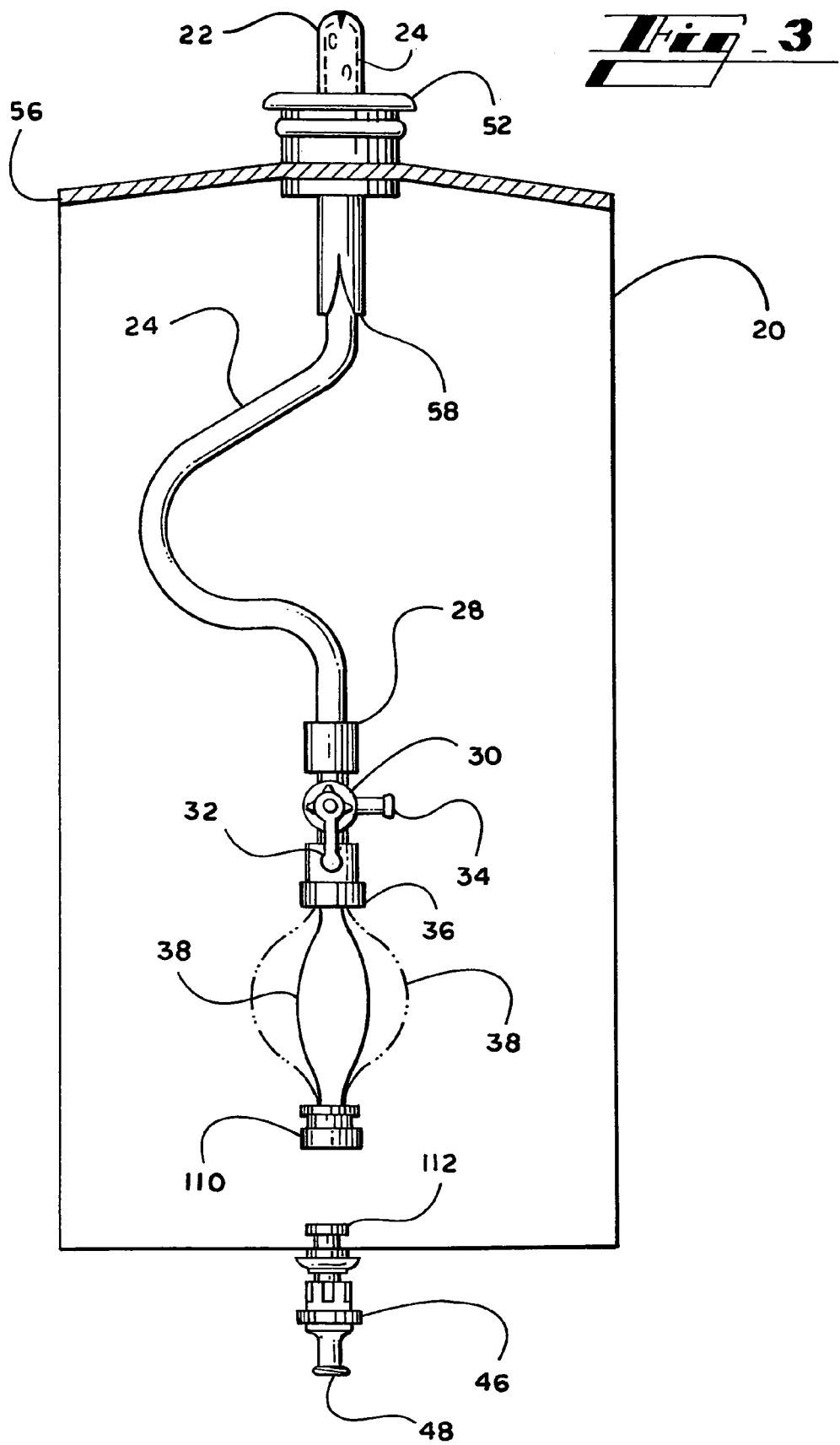
FIG. 3 shows an embodiment of the present invention having a selectively releasable connection between a filling pathway and the fluid storage and delivery device.

In the embodiment shown in FIG. 3, a pass-through connector 112 mounted to the wall of catheter bag 20 is configured to selectively release from a fluid storage and delivery device connector 110. This embodiment uses a one-way valve 46 connected to the pass-through connector 112. The pass-through connector is shown attached to the bottom of the catheter bag 20, but could be located at any position on the catheter bag 20. The fluid storage and delivery device connector 110 is initially connected to the pass-through connector 112. The fluid storage and delivery device connector 110 must also have a one-way valve associated therewith. An apparatus capable of pressurizing the fluid storage and delivery device 38, a syringe, for example, is used to fill the fluid storage and delivery device 38. Once filled, the connection between the fluid storage and delivery device connector 110 and the pass-through connector 112 is released to free the catheter tube 24 for insertion into the patient. The one-way valve associated with the fluid storage and delivery device connector 110 prevents the contents of the fluid storage and delivery device from emptying into the catheter bag 20 after the connection between the fluid storage and delivery device connector 110 and the pass-through connector 112 is released. Such a releasable connection may be threaded or a luer lock connector, or formed of weakened material that can be broken away.

Figure 4:
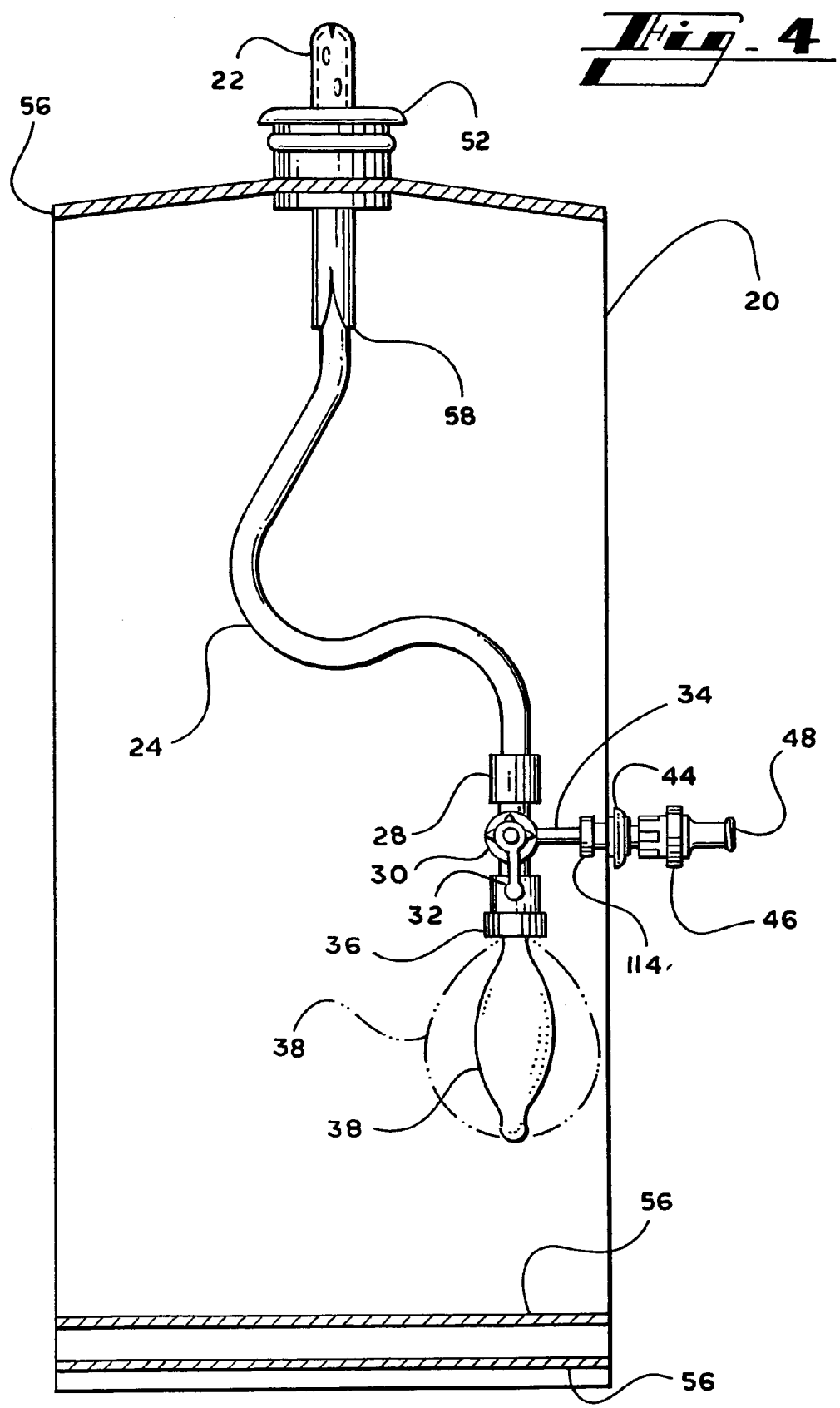
FIG. 4 shows an embodiment of the present invention wherein the urine drainage port of the multi-position valve is also used for filling the fluid storage and delivery device.

In still another embodiment of the invention, the multi-position valve 30 has a position for filling of the fluid storage and delivery device 38, via either a tube extending outside of the bag, or directly via the valve itself. In the latter case, one port of the multi-position valve 30 is accessible from outside of the bag. Filling is accomplished through an additional port on the multi-position valve or the same port that is used for draining urine into the bag. FIG. 4 depicts an embodiment where the same port used for draining urine into the bag (i.e. port 34) is also used for filling the fluid storage and delivery device 38. The port 34 selectively releases at connection point 114 from the pass-through connector 44 so that the end of the catheter tube 24 can ascend in the catheter bag 20 during insertion into the bladder. After filling of the fluid storage and delivery device 38, but prior to releasing the connection between the port 34 and the pass-through connector 44, the valve 30 must be manipulated using valve lever 32 into a position that prevents the contents of fluid storage and delivery device 38 from emptying into the catheter bag 20. In addition, the valve 30 should not be manipulated to pass though the filling position after releasing the connection otherwise the contents of the fluid storage and delivery device will empty into the catheter bag 20. After releasing the connection, the port 34 is then open to the interior of the bag so valve lever 32 on multi-position valve 30 can be manipulated to drain urine from the patient's bladder into the catheter bag 20.

FIG. 5 depicts an embodiment of the invention wherein a portion of the valve 30, in this embodiment the valve lever 32, extends outside of the interior of the catheter bag 20. In this embodiment the valve can be manipulated more easily. This configuration gives direct access to the valve lever 32 so that it can be operated without interference from the catheter bag 20. The multi-position valve 30 is mounted to the wall of the catheter bag 20. A liquid tight seal is formed at point 120 where the multi-position valve 30 or valve lever 32 extends outside of the catheter bag 20. In this embodiment the multi-position valve 30 is mounted toward the top of the catheter bag 20 so that catheter tube 24 can reach a patient's bladder. Alternatively, or in addition, a catheter tube 24 having a longer length is used to ensure that the catheter tube 24 will reach the patient's bladder. If a balloon is used as the fluid storage and delivery device 38, then the length of fill tube 42 should be adequate to allow sufficient space for expansion of the balloon upon filling.

Yet another embodiment is shown in FIG. 6. In this configuration, no fluid storage and delivery device is present in the interior of the bag. Instead, a fill tube 130 connects the multi-position valve 30 to the pass-through connector 44. The fill tube 130 in this embodiment is preferably of larger diameter than the fill tube 42 of the embodiment of FIG. 1 so as not to restrict flow from connector 48 into the multi-position valve. In the embodiment of FIG. 6, a syringe or other fluid delivery device can be attached to the connector 48 and used to deliver fluid into the bladder once the multi-position valve 30 is operated to open the proper fluid pathway from the connector 48 to the catheter tube 24.

FIG. 7 depicts an embodiment of the invention wherein the fluid storage and delivery device is mounted outside of the interior of the catheter bag 20. A tube segment 132 connects the pass-through connector 44 with the fluid storage and delivery device 38. The tube segment 132 is optional as the fluid storage and delivery device 38 can be connected directly to the pass-through connector 44.

Although the above embodiments show a connector 48 for filling the fluid storage and delivery device 38, it should be understood that the device 38 can be filled before sealing the bag for a one-time use. For example, a balloon device 38 could be filled through port 34. In the case of a one-time use configuration, the connector 40, tube 42, connector 44, valve 46, and connector 48 are not needed.

In use, the fluid storage and delivery device is filled with antiseptic with or without antibiotic. A protective cap 54 shown in FIG. 1, which maintains the sterility of the catheter until use, is removed to expose the introducer tip 22 and the collar 52. The introducer tip 22 is inserted into the urethra of the patient until the collar 52 makes contact with the patient. Catheter tube 24 is then extended into the patient's urethra until it reaches the patient's bladder. The tube is handled through the bag during extension to prevent the tube from becoming contaminated with bacteria. Once the catheter tube 24 reaches the patient's bladder, urine flows into orifices 26, down the catheter tube 24, and into the catheter bag 20. The catheter bag 20 prevents leakage of urine onto the patient's skin and thereby reduces the risk of infection. Thus far, the operation is similar to that of a prior art O'Neil catheter.

The valve lever 32 is then manipulated from outside of the catheter bag 20 to release the antiseptic and antibiotic contained in the fluid storage and delivery device 38 into the catheter tube 24. The fluid is forced up the catheter tube 24 and out of orifices 26 where it is injected into the bladder.

The bladder preferably has 10–100 mls of antiseptic injected via the device. The catheter is then removed from the patient, preferably by retracting the catheter tube 24 back into the catheter bag 20 as opposed to pulling the entire apparatus away from the patient. Pulling the entire apparatus away from the patient instead of retracting the tube into the bag would expose the catheter tube 20 to the skin of the patient and anyone assisting with catheterization, increasing the risk of infection.

The drugs delivered may include antispasmodics, antiseptics and antibiotics. The advantage with vesicle delivery of antibiotics is that organisms will be killed on direct contact with the organisms as well as organisms being killed after systemic absorption of the antibiotic across the bladder surface. The resulting concentrations of antibiotics will be high in the bladder compared with the gastrointestinal tracts. This should increase the chance of maintaining normal bowel flora as compared to cases where oral antibiotics are administered. The risk of resistant organisms in the community is therefore decreased.

The risk of organisms reaching the kidney is reduced by a decreased bladder tone and by the antiseptic as well as antibiotic. Bladder tone is decreased by the introduction of antispasmodics into the bladder. This reduces the resting pressure in the bladder so that organisms are not pushed from the bladder into the kidneys.

Antibiotics typically taken orally for urinary tract infections may be used in much lower doses when administered into the bladder. By introducing antibiotics to the bladder in this manner, the amount of antibiotics required is reduced by at least half, and reductions in dosage to 1/10 of current common dosages or less are possible. Therefore, another aspect of the present invention provides a method of treating or inhibiting bladder infections by administering modern antibiotics that in the past commonly have been taken orally for urinary tract infections (for example, cephalosporins) directly to the bladder in smaller doses than when administered orally. Modern antibiotics commonly taken orally for urinary tract infections, such as cephalosporins, have not previously been used in the bladder. It is believed that uses of such antibiotics are less likely to lead to the growth of resistant organisms in the intestine when administered through the bladder. Also, such antibiotics are administered in much smaller doses when delivered directly into the bladder. According to the invention, at least a one-half reduction in dose size is realized, and preferably a 90% or greater reduction.

In practice the interval between catheterization determines the risk of infection. Bacterial growth over time is exponential. As such, the number of organisms in the bladder may increase according to the chart below:

| | Time Since Last Catheterization | | |
| --- | --- | --- | --- |
| | 4 Hours | 6 Hours | 8 Hours |
| Number of Organisms Present in Bladder | $2^3 \rightarrow 2^6 \rightarrow 2^9 \rightarrow 2^{12}$ | $2^{15} \rightarrow 2^{18}$ | $2^{21} \rightarrow 2^{24}$ |

Therefore, when the patient sleeps the risk over 8 hours may be $2^{12}$ greater than when he is catheterizing 4–6 hourly during the day.

It should be noted that the fluid storage and delivery device may be filled in a number of ways. Filling may occur at the time of manufacture before the catheter bag is sealed. Alternatively, the fluid storage and delivery device may remain unfilled so that the drugs to be used may be selected at a later time, which may extend the shelf life of the device. Options for later filling of the fluid storage and delivery device include: filling via a tube that extends through the bag, using a resealable bag that allows direct filling of the fluid storage and delivery device, and using a break away connection to the fluid storage and delivery device that provides external access to enable filling. The break away connection allows the drug storage and delivery device to be filled externally of the bag while also allowing it to ascend inside the catheter bag during insertion of the catheter tube into the patient's bladder. In other embodiments the fluid storage and delivery device 38 is located outside of the catheter bag 20 where it can be filled. Alternatively, medication can be delivered via a syringe or other fluid delivering device outside of the catheter bag 20 by way of a direct fluid pathway to the multi-position valve, as in the embodiment shown in FIG. 6.

If the fluid storage and delivery device 38 is to be filled prior to sterilization of the catheter device and bag, the drugs used are preferably stable following exposure to radiation or gas commonly used during sterilization procedures. The integrity of the fluid storage and delivery device must also be stable following sterilization. That is, the device must not materially deteriorate when exposed to the types and amount of radiation commonly used for sterilization, nor on contact with ethylene oxide or other sterilizing agents.

Another aspect of the present invention relates to the need of more patients to be catheterized more frequently than they need to receiver medication via the bladder. This problem can be solved by the use of one or more catheters that do not have drug delivery mechanisms, such as an O'Neil catheter, in conjunction with one or more catheter systems that do have delivery mechanisms for delivering drugs to the bladder. A kit may be provided which includes one or more new O'Neil drug delivering catheters according to the present invention alternating in use with regular O'Neil catheters. The kit would include some multiple of regular O'Neil catheters per each drug delivering O'Neil catheter. The proper ratio may be determined empirically through testing in patients and may vary depending on the disease and the medication(s) in question. The proper ratio may also vary with the patient's susceptibility to infection. Preferably, a new kit involves one special catheter for antibiotic/antiseptic injection just before bedtime. The drug delivering catheter is used just before the patient goes to sleep because the longer interval between catheterizations increases the number of organisms in the bladder and the risk of infection. The kits therefore have, for example, one special catheter per three (3) regular O'Neil catheters.

The invention thus also relates to bypassing organisms to the maximum extent via the O'Neil catheter and the killing of any contamination once per day via this new method and instrument.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A device comprising:
   a container defining an interior portion, said container having at least one opening;
   a tube having a first end and a second end, said first tube end slideably passing through the at least one opening of the container, said second tube end being disposed within the interior portion of the container;
   a valve at least partially disposed within the interior portion of the container, the valve having at least three ports, a first port being connected to the second tube end, a second port being open to the interior portion of the container;
   the valve being operable from outside of the container to selectively open a fluid pathway between a third port of the valve and the first port of the valve.

2. The device of claim 1 wherein the valve is disposed completely within the interior portion of the container.

3. The device of claim 1 wherein a fluid storage cavity is connected to the third port of the valve.

4. A device comprising:
   a container defining an interior portion, said container having at least one opening;
   a valve disposed at least partially within the container;
   a tube slideably passing through the at least one opening of the container, the tube defining a fluid pathway between the valve and a distal end of the tube;
   a fluid storage cavity in fluid connection with the valve;
   the valve being operable from outside of the container to selectively allow the flow of fluid from the fluid storage cavity into the tube.

5. The device of claim 4, wherein the valve is completely disposed within the container.

6. The device of claim 4, wherein the fluid storage cavity is disposed within the container.

7. The device of claim 4, wherein the container is a bag.

8. The device of claim 7, wherein the bag is a resealable bag.

9. The device of claim 4, wherein the valve has at least three ports, a first of said ports being connected to the tube, a second of said ports being open to the interior of the container, a third of said ports being in fluid connection with the fluid storage cavity.

10. The device of claim 4, wherein the valve has at least three ports, a first of said ports having a fluid pathway to the tube, a second of said ports having a fluid pathway to the interior portion of the container, a third having a fluid pathway to the fluid storage cavity.

11. The device of claim 4, wherein the valve is further operable to selectively allow the flow of fluid through the tube and into the container.

12. The device of claim 4, further comprising a second tube having first and second ends, said second tube being a fill tube, the first end of the fill tube being connected to the fluid storage cavity, the second end of the fill tube allowing the fluid storage cavity to be filled from outside of the container.

13. The device of claim 12, further comprising a second valve connected to the second end of the fill tube, the second valve being a one-way valve to allow fluid to pass into, but not out of the fluid storage device.

14. The device of claim 4, wherein the fluid storage cavity comprises a balloon.

15. The device of claim 4, wherein the fluid storage cavity comprises a syringe.

16. The device of claim 4, wherein the fluid storage cavity comprises a squeezably deformable container.

17. A method of treating a patient comprising the steps:
   providing a catheter having a rube and a bag, a first end of the tube being in the bag;
   inserting a second end of the tube into the patient's urethra;
   draining the patient's bladder into the bag through the tube;
   injecting a volume of fluid into the patient's bladder through the tube without piercing the bag, and without removing the first end of the tube from the bag.

18. The method of claim 17, further comprising the step: draining the patient's bladder on at least one other occasion during a day without injecting medication into the bladder.

* * * * *

UNITED STATES PATENT AND TRADEMARK OFFICE
CERTIFICATE OF CORRECTION

| | | |
|---|---|---|
| PATENT NO. | : 7,150,739 B2 | Page 1 of 1 |
| APPLICATION NO. | : 10/686026 | |
| DATED | : December 19, 2006 | |
| INVENTOR(S) | : O'Neil | |

It is certified that error appears in the above-identified patent and that said Letters Patent is hereby corrected as shown below:

<u>Claim 16 Column 10,</u>
Line 26, "rube" should read --tube--.

Signed and Sealed this

Tenth Day of April, 2007

JON W. DUDAS
*Director of the United States Patent and Trademark Office*